United States Patent [19]

Findl et al.

[11] 4,428,366

[45] Jan. 31, 1984

[54] ELECTROMAGNETIC APPARATUS AND METHOD FOR THE REDUCTION OF SERUM GLUCOSE LEVELS

[75] Inventors: Eugene Findl, Amityville; Peter O. Milch, Coram, both of N.Y.

[73] Assignees: Alfred B. Kurtz, Wynnewood, Pa.; Robert J. Kurtz, New York, N.Y.

[21] Appl. No.: 261,257

[22] Filed: May 6, 1981

[51] Int. Cl.³ .............................................. A61B 17/52
[52] U.S. Cl. ........................................................ 128/15
[58] Field of Search .................................. 128/1.3–1.5, 128/804

[56] References Cited

U.S. PATENT DOCUMENTS 3,658,051 4/1972 MacLean ............................ 128/1.5

Primary Examiner—Kyle L. Howell
Assistant Examiner—Francis J. Jaworski

Attorney, Agent, or Firm—Larson and Taylor

[57] ABSTRACT

Apparatus and a non-invasive technique are disclosed for the control of glucose levels in living animals afflicted with hyperglycemia. The apparatus is used to apply a uniform, monopolar pulsed magnetic field to cause electric currents and field generation in the animal. The pulsed magnetic fields are obtained by transmitting individual pulses of direct current to Helmholtz coils located on opposite sides of the animal. The optimum pulse train configuration for the test animals, which were a breed of white rats, is a pulse repetition rate of 15 hertz, a pulse amplitude of 60 millivolts, and a pulse width of 350 microseconds. The generated field in the preferred embodiment was about 15 gauss. Although the treated rats did not have a normal serum glucose level, the depicted serum glucose levels are significantly lower than those of the control animals.

8 Claims, 17 Drawing Figures

ELECTROMAGNETIC APPARATUS AND METHOD FOR THE REDUCTION OF SERUM GLUCOSE LEVELS

FIELD OF THE INVENTION

The present invention relates to the treatment of living animals afflicted with hyperglycemia for reducing the same. In particular, the present invention relates to apparatus and a method for decreasing the serum glucose level of living animals by the application of pulsed magnetic fields.

For over a century, attempts have been made to utilize electric currents for medical purposes. Many of these attempts were in the hands of charlatans who made claims for "curing" practically every disease known to mankind. Consequently, the scientific community greets most new therapeutic developments involving electric currents and magnetism with some skepticism.

Recently, however, a slow but definite shift toward a better understanding of bioelectric phenomena has been occurring. Some of the recent work has shown that electric or electromagnetic fields may be helpful or harmful, depending upon the particular field and the particular effect being studied. For example, some Soviet workers have reported on the deleterious effects from alternating magnetic fields of industrial frequency (i.e, 50 to 60 hertz). Kolesova et al, "Pathogenesis of Insulin Deficiency Induced By Alternating Magnetic Field Of Industrial Frequency." 6 Patologicheskaia Fiziologia I Eksperimentalnaia 71 (1978). In particular, the Kolesova et al article reported that in experiments on rats a single action of alternating magnetic field having an intensity of 200 Oe and a frequency of 50 Hz for a 24 hour exposure led to the development of a relative insulin deficiency. Multiple action of the alternating magnetic field (e.g., 6.5 hours per day for 5 days) favored development of an absolute insulin insufficiency.

On the other hand, some scientists have found that there are beneficial effects of electromagnetic fields on congenital pseudarthroses. Bassett et al, "A Non-Operative Salvage of Surgically Resistant Pseudarthroses and Non-Union by Pulsing Electromagnetic Fields". 124 Clin. Orthopaedics 128 (1977). These same authors wrote an article describing the enhancement of the repair of canine osteotomies by the application of low frequency, pulsing electromagnetic fields. Bassett et al, "Augmentation of Bone Repair by Inductively Coupled Electromagnetic Fields," 134 Science 575 (May, 1974). This article describes the use of pulsating magnetic fields produced by air-gap, rectangular coils to induce dynamic, orthogonal voltage fields in bone and soft tissue. Pulses of 1 millisecond duration with a 1 hertz frequency and of 150 microsecond duration with a 65 hertz frequency were used and resulted in augmented bone repair. A similar type of treatment was the subject of the U.S. Pat. No. 4,105,017 to Ryaby et al. This patent discloses the use of a pulse train having pulses with both a positive and a negative portion having a pulse repetition rate between 10 and 100 hertz with an average amplitude of 10 millivolts and a pulse duration of less than 1 millisecond.

Other United States patents have issued which claim that the use of magnetic, electrical and electromagnetic fields induces the stimulation of endocrine glands. These patents include the MacLean U.S. Pat. No. 3,658,051; the Elmi U.S. Pat. No. 3,337,776; Smith et al U.S. Pat. No. 3,566,877; Manning U.S. Pat. No. 3,893,462; and Edwards U.S. Pat. No. 3,056,409. However, none of these patents are expressly directed to the reduction of serum glucose levels through the electromagnetic stimulation of the living animal, although some of the patents, for example the MacLean patent makes broad claim for the cure of all diseases, including the stimulation of endocrine systems. These cure all approaches are not supported with scientific data, on the one hand, and use a different method than that presented in the present application.

More particularly, experiments by others and experiments by the present inventors have shown that the specific waveform generated by the electromagnetic is very critical to the biomedical results. For example, experiments done at the Pettis Memorial VA Hospital, Loma Linda, Calif., showed that there was a *decrease* in insulin production by using a pulsed magnetic field that differed from the field disclosed hereinbelow.

It has been repeatedly stated that there is the need for the non-invasive treatment of diabetes which would result in the lowering of the serum glucose levels of the treated animals. Furthermore, there is the need for apparatus that is portable and that can be adjusted so as to accommodate patients outside of a medical establishment.

SUMMARY OF THE INVENTION

The present invention provides a non-invasive technique and apparatus for the control of glucose levels. Furthermore, there is disclosed a need for the treatment of diabetes that may reduce and/or eliminate the need for insulin.

Apparatus according to the present invention for alleviating hyperglycemia in living animals afflicted with same comprises an electromagnet and an electric power supply means. The electromagnet has an air gap configuration so as to produce a substantially uniform magnetic field. The electric power supply means supplies a low frequency, pulsating power to the electromagnet so as to produce a relatively low magnetic field from about 5 to 100 gauss. The power supply means comprises, in turn, a means for producing a wave train of pure, unmodulated pulses having a pulse repetition rate between at least 5 hertz and 75 hertz and a pulse width and pulse amplitude selected so as to cause a decrease in the serum glucose level of the animal to be treated.

The method of treating an animal having hyperglycemia comprises placing at least a portion of the animal in the field of an electromagnet. The portion is then subjected to a pulsating, magnetic field generated by the electromagnet. The magnetic field is generated by providing the electromagnet with an intermittent power supply that produces a wave train of pure, unmodulated pulses. The pulse repetition rate of the pulse train, pulse width and pulse amplitude of the pulses are selected so as to cause a decrease in the serum glucose level of the animal.

In one preferred embodiment the electromagnet and the pulse amplitude are also selected so as to produce a low level, low frequency magnetic field of not more than 100 gauss. The electromagnet is spaced from the portion of the animal so as to create an air gap there between. The magnetic field is substantially uniform.

In another preferred embodiment of the present invention for alleviating hyperglycemia in rats, the rats are subjected to a pulsed, substantially uniform magnetic field in which the pulses have a pulse width of 350 microseconds and are applied at a frequency of about 15 hertz.

Other objects and advantages of the present invention will be set forth in or become apparent from the detailed description of the presently preferred embodiments described hereinbelow.

DETAILED DESCRIPTION OF THE PREFERRED EMBODIMENTS

Figure 1:
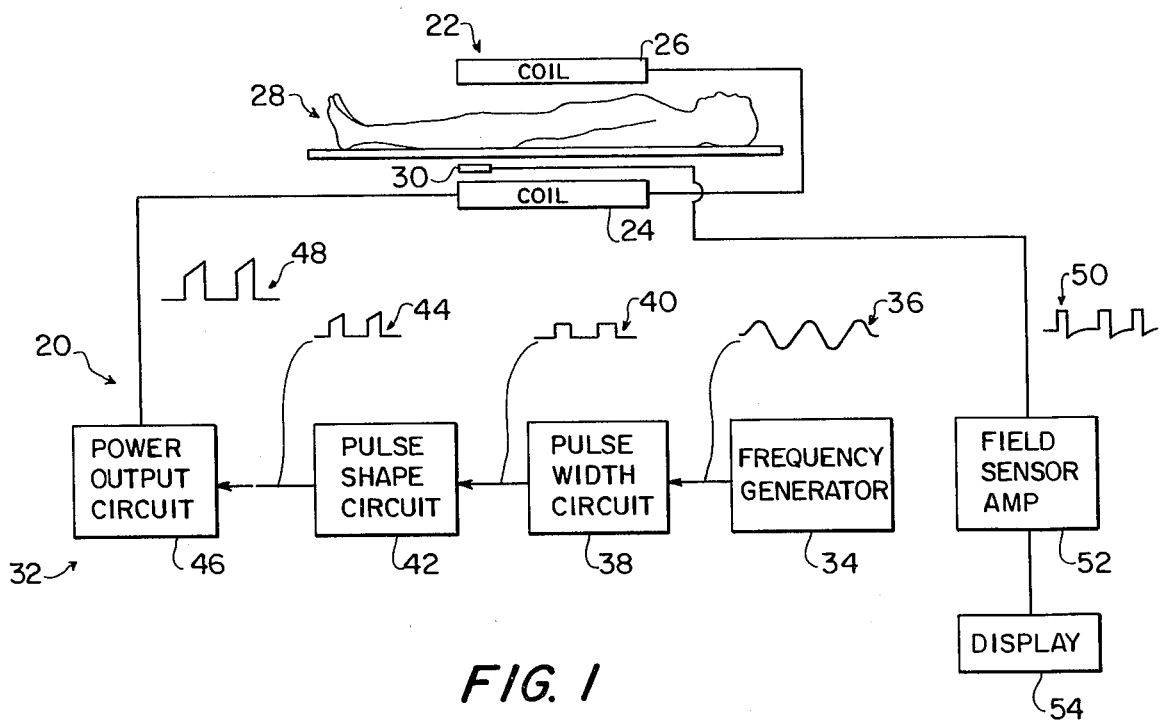
FIG. 1 is a schematic representation showing one embodiment of the present invention for reducing the serum glucose levels of a living animal.

With reference now to the figures wherein like numerals represent like elements throughout the several views, and in particular with reference to FIG. 1, an electromagnetic apparatus 20 for reducing serum glucose levels in living animals is depicted. Apparatus 20 is comprised of an electromagnet 22 having two, spaced apart, coaxially mounted coils depicted schematically at 24 and 26 above and below a patient treating station 28. Electromagnet 22 is discussed in greater detail hereinbelow. In general, however, electromagnet 22 has an air gap configuration that produces a substantially uniform magnetic field. Such a field is produced, for example, by a pair of Helmholtz coils. Located at patient treating station 28, between coils 24 and 26, is a sensor 30 for measuring the resultant electric field. For exemplary purposes, a living animal patient, in this case a human being, is depicted as being positioned with coils 24 and 26 located above and below the abdomen region where the pancreas is located.

Apparatus 20 also includes an electric power supply means 32 electrically connected to electromagnet 22 for supplying low frequency, monopolar pulsating power. In the embodiment of FIG. 1, power supply means comprises a frequency generator 34 which produces a sinusoidal wave output depicted at 36. Frequency generator 34 can be any one of a number of commercially available, conventional frequency generators having an adjustable output frequency. The output of frequency generator 34 is coupled to a pulse width circuit 38 that converts the sinusoidal wave into a wave train having a plurality of pulses, such as indicated by wave 40. Pulse width circuit 38 is conventional and includes a means for adjusting the pulse width. The output of pulse width circuit 38 is fed to the input of a pulse shape circuit 42 in which the desired pulse shape can be produced. The output wave from pulse shape circuit 42 is indicated at 44 and is fed into the input of a power output circuit 46. Power output circuit 46 is a conventional amplifying circuit in which the pulse amplitude can be adjusted. The output wave from pulse output circuit 46, indicated at 48, is connected in series to coils 24 and 26. The generated magnetic field is detected by sensor 30 and a typical detected waveform is indicated at 50. The output from sensor 30 is connected to a conventional field sensor amplifier 52, which in turn is connected to a conventional display 54. Display 54 can simply be a conventional oscilloscope.

Power supply means 32 thus provides a pulse train or wave of power to electromagnet 22 in which the shape, amplitude, and frequency of the pulses can be adjusted. Pulse train 48 is shown in greater detail in FIG. 1a and consists of a plurality of pure, unmodulated pulses 52. By this it is meant that pulses 52 are not wave packets or packets or pulses, but rather are individualized, single pulses. It is well known that the shape of the output pulse from electromagnet 22 will differ from the shape of the input power thereto because of the inductive load from coils 24 and 26. For this reason, in the embodiment of FIG. 1, the shape of the applied pulse 52 is selected so as to produce a squared-off top of the detected pulses 54 of detected wave train 50.

Figure 1A:
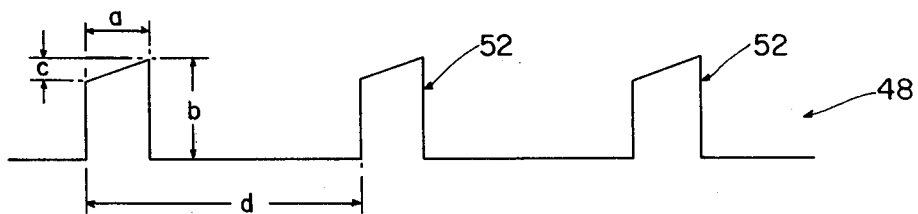
FIG. 1a and FIG. 1b are enlarged graphs showing respectively a waveform as applied to the magnetic coils and as detected by a magnetic field sensor.
Figure 1B:
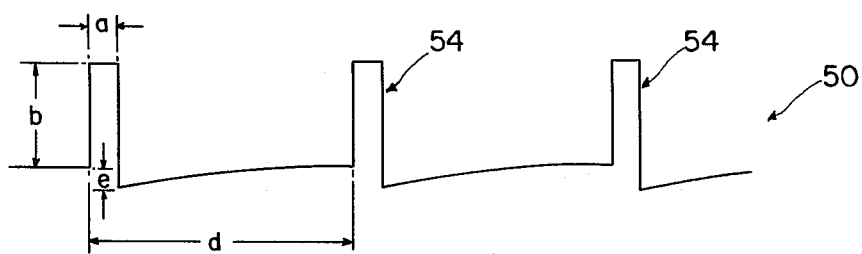

The effect of electromagnet 22 on the pulse shape is shown in FIGS. 1a and 1b where the applied pulse 52 and the detected pulse 54 are respectively shown. Pulses 52 and 54 can be described through various, conventional components. Each pulse has a pulse width "a" measured in seconds or microseconds, a pulse magnitude or amplitude "b" measured in volts or millivolts, a ramp magnitude "C" measured in volts or millivolts, and a cycle time or period measured in seconds or milliseconds. In addition to a positive amplitude "b", detected pulse 54 also has a negative magnitude or amplitude "e" which results from the collapsing magnetic field of electromagnet 22 at the end of each applied pulse 52. By supplying a positive ramp in applied pulse 52, it can be seen that the shape of detected pulse 54 can be squared-off.

Figure 2:
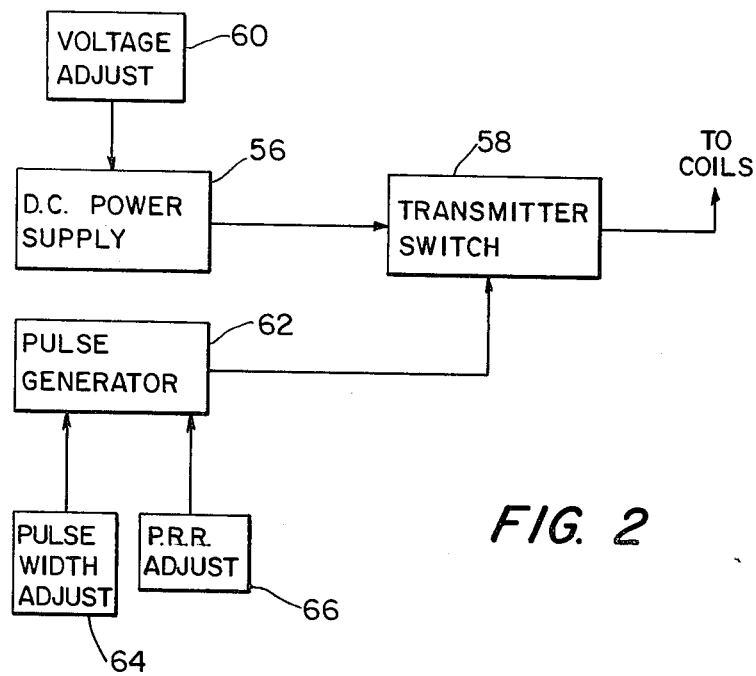
FIG. 2 is a schematic electrical block diagram showing an alternate embodiment for generating the pulsating electric power applied to the coils.
Figure 3:
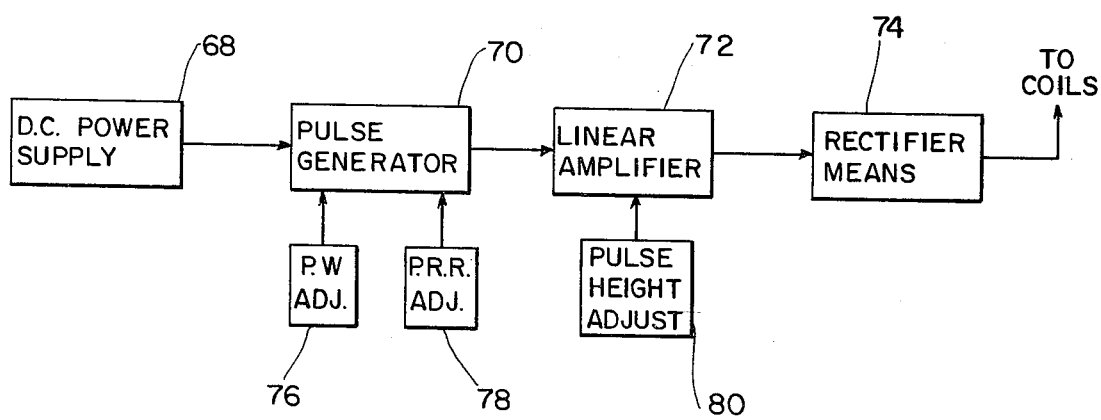
FIG. 3 is a schematic electrical block diagram showing a further newly supply for providing the pulsed electrical power for the coils.

Although the particular pulse train and pulse shape are critical features of the present invention, the particular means for producing the pulse train can have different embodiments. Other embodiments of power supply means 32 are depicted in FIGS. 2 and 3. In FIG. 2, a DC power supply 56 provides power to a high current, conventional transistor switch 58, the output of which is connected to electromagnet 22, (not shown). A voltage adjustment 60 can vary the amount of the DC voltage output from power supply 56, and thus vary the ultimate pulse amplitude of the applied pulse 52. Transistor switch 58 is turned on and turned off by a pulse train produced by a conventional pulse generator 62. Pulse generator 62 has a pulse width adjustment 64 and a pulse repetition rate adjustment 66. Thus, a low power, accurately controllable pulse train can be inexpensively generated to control transistor switch 58. In this way, the full high current applied to electromagnet 22 does not flow through pulse generator 62.

With respect to FIG. 3, a third embodiment of power supply means 32 is depicted. A DC power supply 68 that can be the same as power supply 56, feeds a pulse generator 70, which can be the same as pulse generator 62. The output of pulse generator 70 is fed to the input of a conventional linear amplifier 74. A rectifier means 72 as connected between amplifier 74 and the electromagnet and can be any conventional circuit such as a diode clamp or a conventional diode rectifier to ensure that the generated pulse train from pulse generator 70 is basically monopolar. What is meant by monopolar is that the pulse train has its major components in only one direction from the zero base line. However, whether the pulse is positive or negative only affects the direction of the resultant magnetic field and does not seem to be a major consideration. Pulse generator 70 also has a pulse width adjustment 76 and a pulse repetition rate adjustment 78. The amplitude of the applied pulses is varied by a pulse height adjustment 80 connected to linear amplifier 74.

Obviously, other configuration of power supply means 32 are possible, just so long as the critical features of the pulse train can be achieved.

Figure 4:
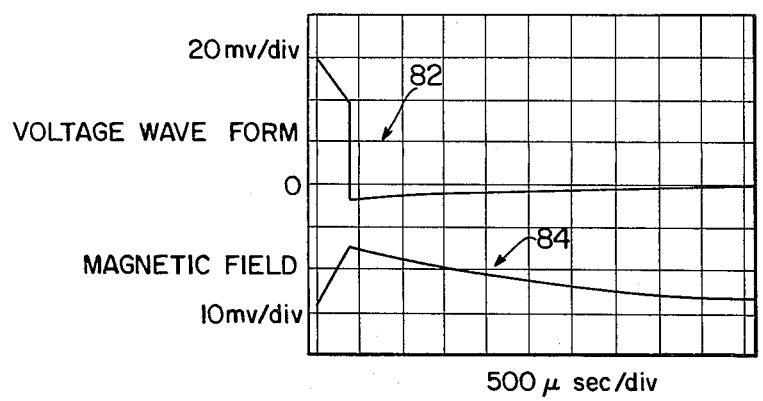
FIG. 4 is a graph of another electrical waveform applied in experiments conducted using the present invention and depicting the resultant magnetic field.

A typical stimulation waveform which was actually detected is depicted in FIG. 4. The upper waveform 82 is the detected voltage from a pickup coil 30 placed between electromagnet coils 24 and 26. As measured by this coil, positive pulse height is 60 millivolts and positive pulse width is 350 microseconds. The negative portion of the pulse is present because of a diode clipping arrangement. The negative portion of the curve is about one-tenth the pulse height or about 6 millivolts. The lower waveform in FIG. 4, denoted 84, is the magnetic waveform detected by a Hall effect sensor 94. Peak magnetic field is about 15 gauss. The embodiment of the power supply means 32 depicted in FIG. 3 was used to produce the waveforms of FIG. 4 when connected to an electromagnet such as that depicted in FIG. 5.

Figure 5:
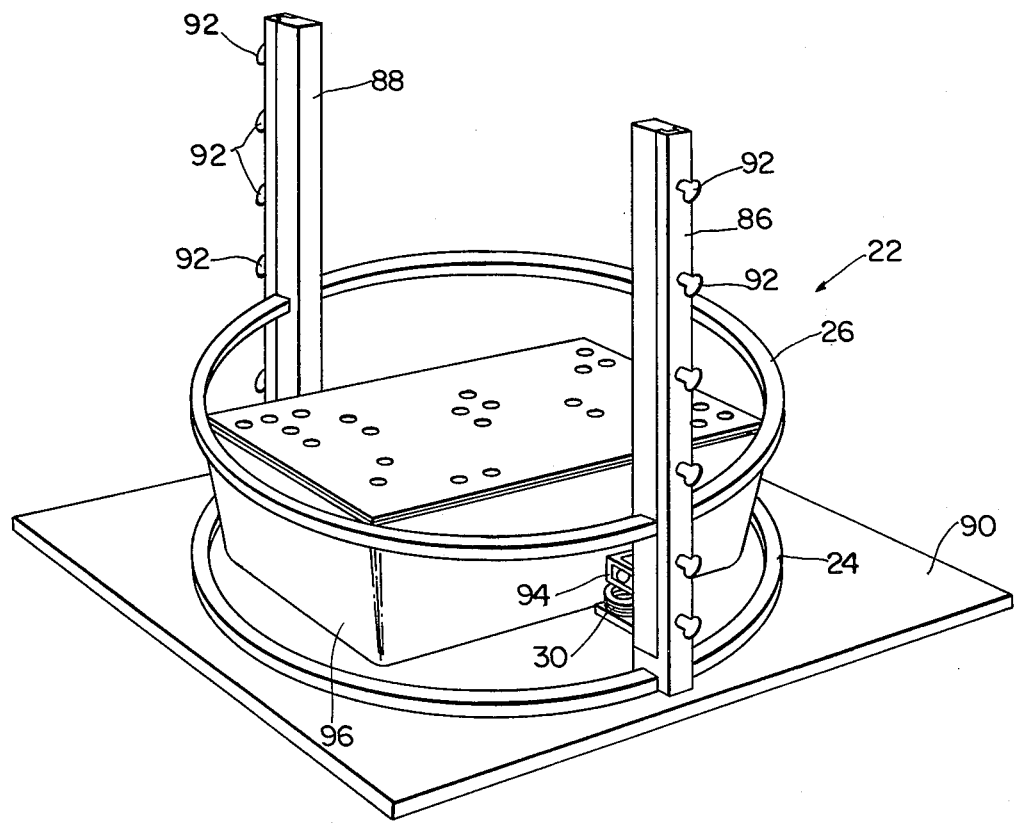
FIG. 5 is a perspective view of an electromagnet used in experiments conducted using the present invention.

Turning now to FIG. 5, electromagnet 22 is a conventional Helmholtz coil type electromagnet. Electromagnet 22 is comprised of lower coil 24 and upper coil 26 mounted in two opposed, vertical mounting members 86 and 88. Lower coil 24 is permanently mounted at the bottom of mounting members 86 and 88 on an insulated base 90. Mounting members 86 and 88 contain a plurality of set screws 92 for adjustably mounting upper coil 26. Hall effect sensor 94 is depicted mounted to mounting member 86 and a voltage coil sensor 30 for generating voltage waveform 82 is mounted immediately above sensor 94. In the experimental tests of the present invention, white rats are used and kept in a plastic cage 96 mounted on base 90 between coils 24 and 26.

Coils 24 and 26 have an inner diameter of 46 centimeters and are made of 14 gauge copper magnet wire that is coated with a resin for rigidity. Mounting members 86 and 88 and base 90 can be made of a non-magnetic material, such as an acrylic plastic. Similarly, cage 96 is made of a non-magnetic material such as an acrylic plastic. Voltage sensor 30 is one centimeter in diameter is made of $62\frac{1}{2}$ turns of 26 gauge copper wire.

As is well known, the use of a Helmholtz coil type electromagnet produces a substantially uniform magnetic field throughout the distance between the two coils and throughout radial slices therebetween. The optimal arrangement in a Helmholtz coil is with the coils spaced apart a distance equal to the diameter of the same coil. As shown in FIG. 5, coils 24 and 26 are flat circular coils and, as mentioned above, have an equal number of turns and equal diameters. Coils 24 and 26 are arranged about a common axis, (i.e., are coaxial) and are connected in series to have a common current. Although the present embodiment is depicted with two coils, it should be obvious that a relatively uniform field will also be produced with a signal coil, but will be less effective.

The following examples describe the application of the present invention to treat a patient having hypoglycemia.

EXAMPLE 1

Male and female albino rats, weighing between 250 to 550 grams were used in this example. The breeding colony was derived from two different strains of Sprague-Dawley rats initially bred in 1977 and 1978. The rats were made diabetic by the IM injection of streptozotocin in the amount of 45 milligrams per kilogram of rat body weight. The injections were given 3 days before they were used in the experiment. Half of the rats formed the test group and were placed in cages, such as cage 96 depicted in FIG. 5, and subjected to an electromagnetic field. The other half of the rats were kept under similar conditions as a control group, but outside of an electromagnetic field. All the rats were kept overnight without food, but unlimited water. The test group of rats were subjected to the particular electromagnetic field, described hereinbelow, during the entire night.

The next morning, all of the rats were given a two hour glucose tolerance test. Blood samples of approximately 0.5 milliliters were taken from the tip of the tail of each rat at times: 0, 30 minutes, 60 minutes, and 120 minutes after an oral glucose load of 3 grams glucose per kilogram of rat body weight was administered in a 50% solution directly into the stomach of the rat. The serum was separated by centrifugation and serum glucose concentrations were determined using a YSI Glucose Analyzer.

Figure 6:
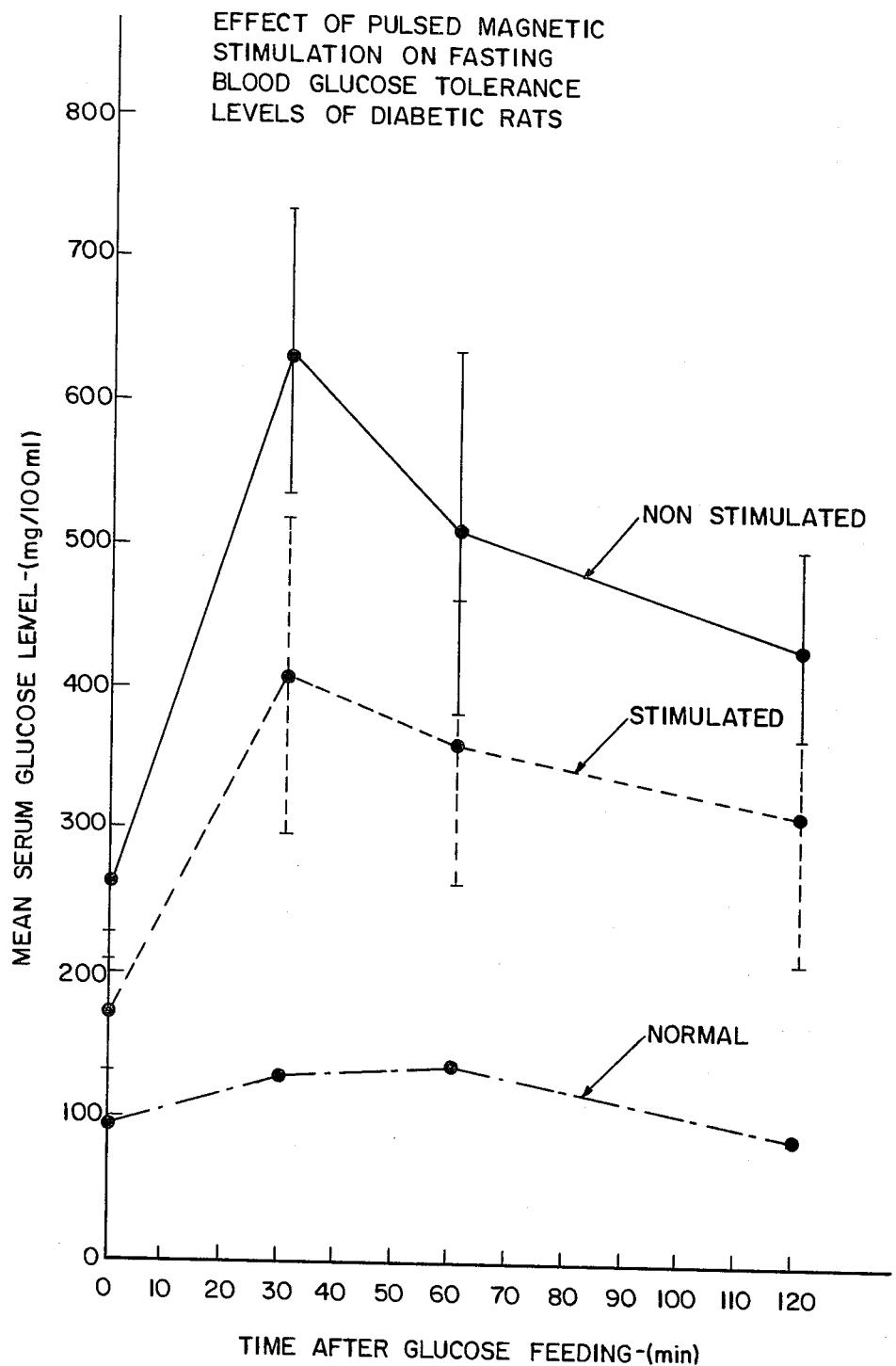
FIG. 6 is a graph of the results of the serum glucose levels of diabetic rats treated and not treated by the present invention.

In this example, the pulse amplitude was adjusted to 60 millivolts, pulse width of 350 microseconds and frequency set at 15 hertz. The results are shown in FIG. 6. These results are actually the average of results obtained from 18 diabetic rats which were stimulated compared with 18 diabetic rats that were not stimulated by the magnetic field. Although the treated rats are not down to normal levels, their serum glucose levels are significantly lower than those of the control rats.

As mentioned above, the waveform as seen by sensor 30 is shown in FIG. 4. This waveform was a unipolar train. However, sinusoidally modified monopolar pulses (i.e., have rounded tops) produced similarly statistically significant results.

EXAMPLES 2-4

Figure 7:
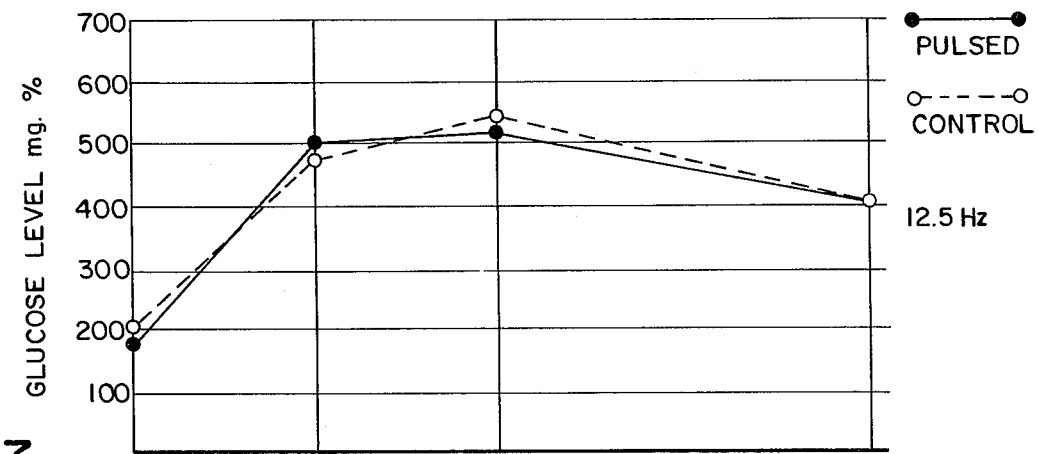
FIGS. 7, 8 and 9 are graphs showing the results of varying the frequency of the power supplied to the magnets.
Figure 8:
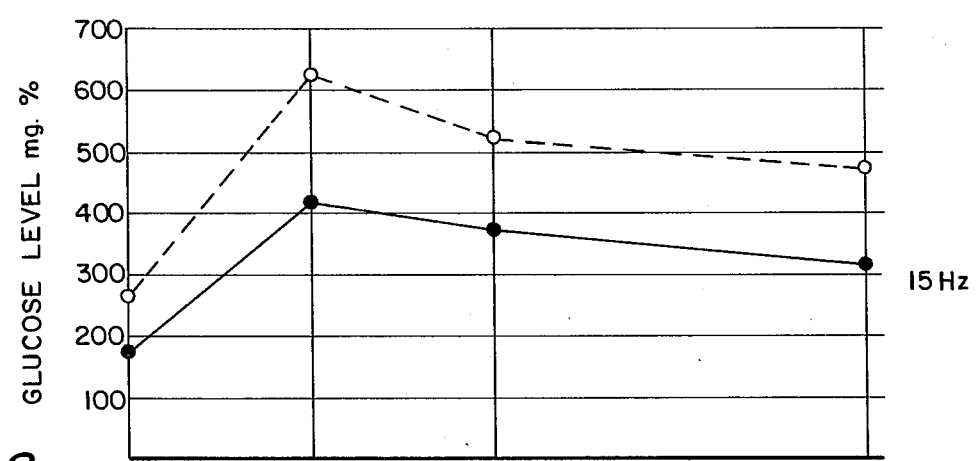
Figure 9:
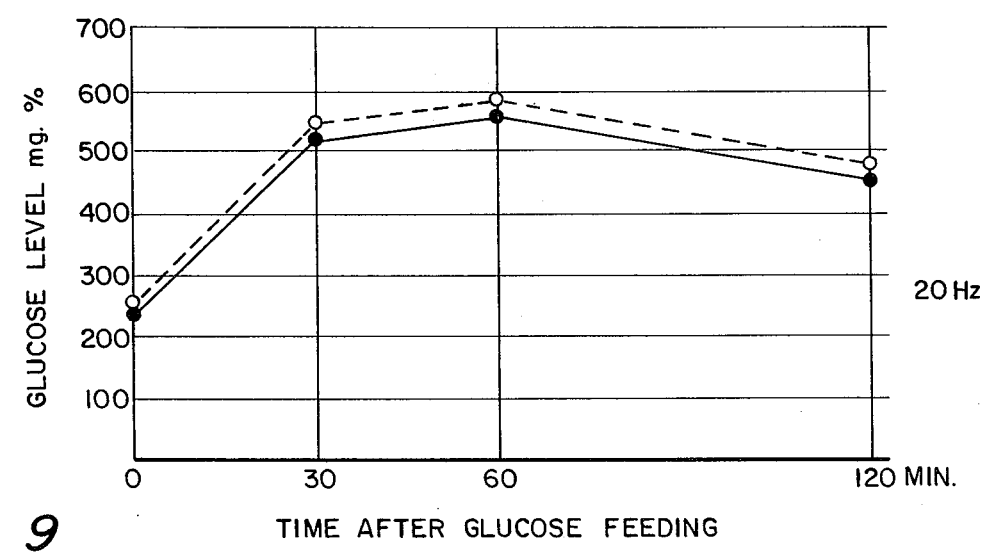
Figure 10:
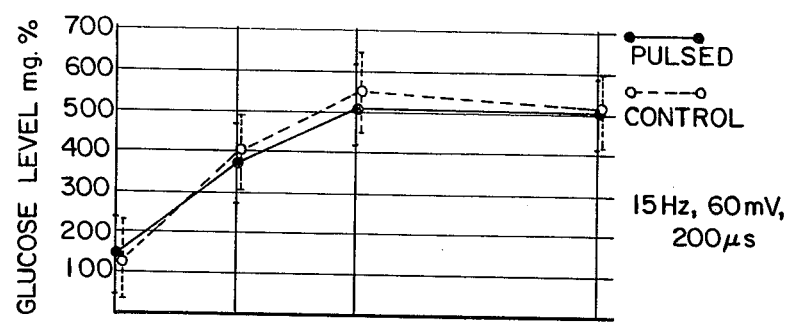
FIGS. 10, 11, 12, 13 and 14 are graphs showing the results of holding the frequency constant, and varying the pulse width of the power supplied to the electromagnets.
Figure 11:
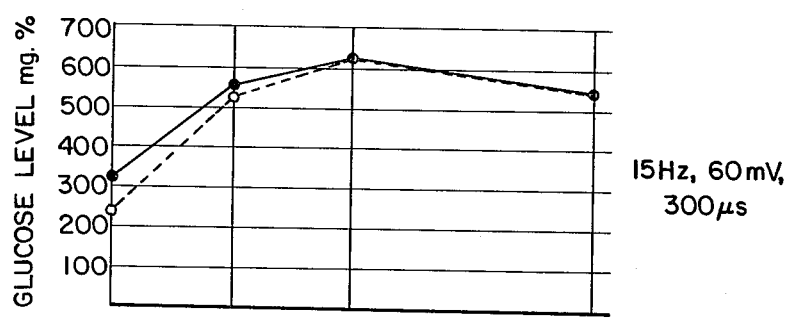
Figure 12:
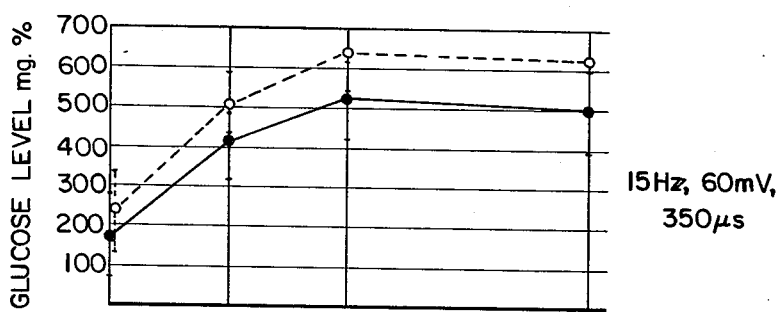
Figure 13:
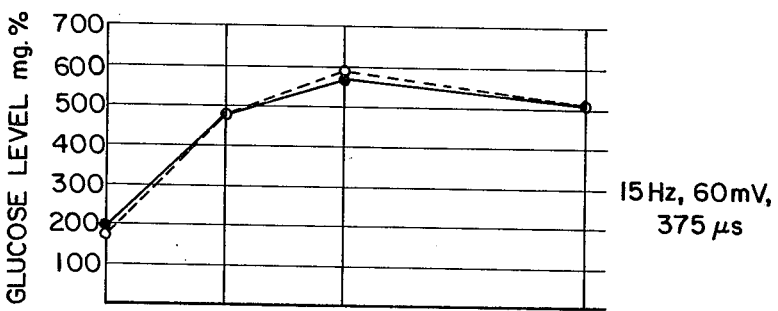
Figure 14:
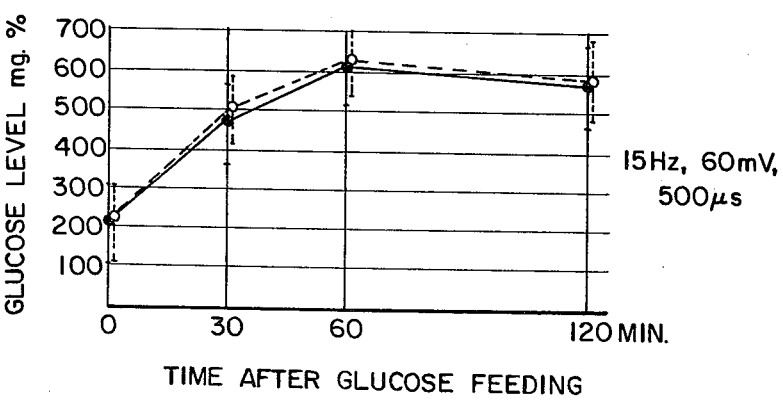

In Examples 2-4, the same controls as mentioned above with respect to Example 1 were used, except that the frequency of the pulse train was varied. The results are shown in FIGS. 7, 8 and 9. These figures show that a relatively small change in the frequency of the pulse train renders the magnetic field ineffective. In fact, other experiments indicated that experiments conducted at 14 hertz and 16 hertz yielded lower serum glucose levels in the exposed rats, but the differences between those and the control animals were not statistically significant.

EXAMPLES 5-9

Examples 5-9 used the same apparatus and controls as mentioned above with respect to Example 1, except that the pulse width was modified as indicated in FIGS. 10-14, respectively. It is clear that only a pulse width of 350 microseconds produces an effective lowering of the serum glucose levels while pulse widths of 200, 300, 375, and 500 were ineffective. A further example using a pulse width of 340 microseconds had borderline effectiveness.

It is thus thoroughly clear that, at least with respect to the tested rats, the sensitivity of the glucose levels to pulse frequency and pulse width has a definite "window". A similar sensitivity of the glucose levels to pulse amplitude has also been preliminarily detected, but experiments at the date of the filing of this application have not progressed sufficiently to include those results. In summary, it appears that the particular pulse train frequency and the particular shape of each pulse (at least with respect to the pulse width and probably the pulse height) are critical in lowering the glucose levels. On the other hand, as mentioned above, other experimenters have reported that they have found an increased glucose level using a signal that differed from that discussed hereinabove.

Other experiments conducted along the same lines for healthy rats indicated that the use of a pulse train at a 15 hertz frequency with each pulse having an amplitude of 60 millivolts and a pulse width of 350 microseconds had no discernible affect.

Although the mechanism of the action of the pulse field is not known, the easiest and most logical explanation is to assume that a particular type of electromagnetic field affects the still existing islets of Langerhans and stimulate the production and/or release of insulin. This could, presumably, be the result of increased ion transport, especially $Ca^{++}$, in the islets. However, other possibilities could include a change in membrane permeability resulting in increased glucose uptake and glucose utilization by body cells, increased glucose excretion by the kidneys, or indirect affects on the insulinglucagon system through other affected hormones (e.g., thyroid and/or adrenal hormones).

In addition, the effect of electromagnetic fields on animals other than rats is not known at the present time. However, through some simple experiments using the criteria outlined hereinabove could easily be conducted to ascertain the critical parameters of pulse frequency, pulse width, and pulse height.

It is also believed that the use of monopolar, uniformly periodic pulses is important to the operation of the mechanism resulting in lowered glucose levels. By uniformly periodic, it is meant that the pulses are equally spaced throughout the measured time period, or referring to FIGS. 1a and 1b, the cycle time "d" is constant.

Figure 15:
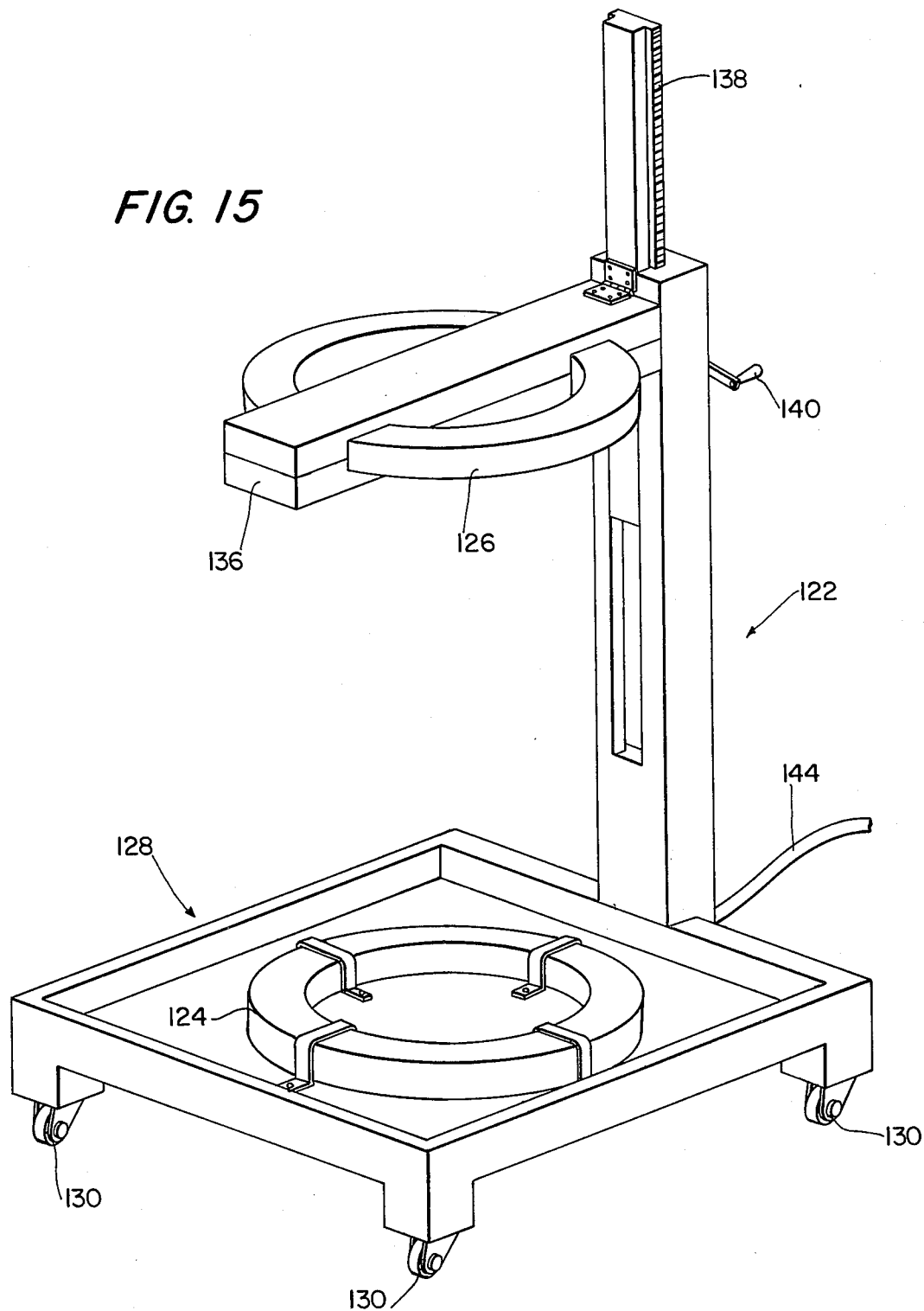
FIG. 15 is a perspective view of yet another embodiment of the electromagnet according to the present invention.

Referring now to FIG. 15, a further embodiment of a Helmholtz-type electromagnet 122 is depicted. Electromagnet 122 is comprised of two, spaced apart, flat circular coils, a lower coil 124 and an upper coil 126. Lower coil 124 is fixedly mounted onto a base 128 which, in turn, is movably mounted on four rollers 130. Upper coil 126 is adjustably mounted on a stand 132. Stand 132 is comprised of an upstanding, substantially vertical member 134 rigidly mounted at one end thereof to base 128 and a substantially horizontal member 136 rigidly mounted onto a rack 138. Rack 138, in turn, fits within a correspondingly shaped bore extending through vertical member 134. A crank 140 engages rack 138 for adjusting the separation between upper and lower coils 124 and 126. As shown in FIG. 15, horizontal member 136 is mounted to rack 138 with a hinge 142 so that it can be folded against vertical member 134 for storage or during transportation. Power is supplied to electromagnet 122 through a power cord 144.

Thus, electromagnet 122 provides an easily transportable and adjustable electromagnet usable with the present invention.

Thus, while the invention has been described in detail with respect to exemplary embodiments thereof, it will be understood by those of ordinary skill in the art that these and other variations and modifications may be effected in the exemplary embodiments within the scope and spirit of the invention.

We claim:

1. A method of alleviating hyperglycemia in a living animal afflicted with same, the method comprising:
    placing at least a portion of the animal in the field of an electromagnet: and
    subjecting at least the portion of the animal to a pulsating magnetic field generated by said electromagnet by providing said electromagnet with an intermittent electric power supply having the following characteristics:
    a pulse train of pulses having a pulse repetition rate of about 15 hertz plus or minus 0.5 hertz, a pulse width of about 350 microseconds and a pulse amplitude of about 60 millivolts to cause a decrease in the serum glucose level of the animal.

2. The method as claimed in claim 1 wherein said magnetic field is a substantially uniform, low level magnetic field of not more than 300 gauss and said electromagnet is spaced from the animal so as to provide an air gap therebetween.

3. The method as claimed in claim 2 wherein said pulse train is monopolar and uniformly periodic and is comprised of pure, unmodulated pulses.

4. The method as claimed in claim 2 wherein said magnetic field strength is from 5 to 30 gauss.

5. The method as claimed in claim 11 wherein said magnetic field is about 15 gauss and is uniform.

6. The method as claimed in claim 1 wherein said pulse train is uniformly periodic.

7. The method as claimed in claim 1 wherein said pulse is monopolar and uniformly periodic and wherein said magnetic field is substantially uniform.

8. The method as claimed in claim 1 wherein said animal is constantly subjected to said magnetic field for a period of time of four to sixteen hours in duration.

* * * * *